(12) United States Patent
Gerlitz et al.

(10) Patent No.: US 9,056,198 B2
(45) Date of Patent: Jun. 16, 2015

(54) LOW LEVEL LASER THERAPY (LLLT) SYSTEMS AND DEVICES

(76) Inventors: Yonatan Gerlitz, Herzliya (IL); Michael Schlosser, Haifa (IL)

(*) Notice: Subject to any disclaimer, the term of this patent is extended or adjusted under 35 U.S.C. 154(b) by 300 days.

(21) Appl. No.: 13/007,057

(22) Filed: Jan. 14, 2011

(65) Prior Publication Data

US 2011/0112613 A1    May 12, 2011

Related U.S. Application Data

(63) Continuation-in-part of application No. 12/534,878, filed on Aug. 4, 2009, now Pat. No. 8,790,382.

(60) Provisional application No. 61/295,039, filed on Jan. 14, 2010.

(51) Int. Cl.
| | |
|---|---|
| *A61N 5/06* | (2006.01) |
| *B23K 26/00* | (2014.01) |
| *B23K 26/06* | (2014.01) |
| *B23K 37/00* | (2006.01) |

(52) U.S. Cl.
CPC ....... *A61N 5/0613* (2013.01); *A61N 2005/0644* (2013.01); *A61N 2005/0651* (2013.01); *A61N 2005/0659* (2013.01); *B23K 26/0006* (2013.01); *B23K 26/0096* (2013.01); *B23K 26/0648* (2013.01); *B23K 37/006* (2013.01)

(58) Field of Classification Search
CPC .............................. A61N 5/06; A61N 2005/06
See application file for complete search history.

(56) References Cited

U.S. PATENT DOCUMENTS

| | | | | |
|---|---|---|---|---|
| 3,186,981 | A * | 6/1965 | De Ronde | 200/318 |
| 5,060,658 | A | 10/1991 | Dejter, Jr. et al. | |
| 5,551,437 | A | 9/1996 | Lotscher | |
| 5,663,828 | A * | 9/1997 | Knowles et al. | 359/237 |
| 5,997,531 | A * | 12/1999 | Loeb et al. | 606/13 |
| 6,306,160 | B1 * | 10/2001 | Nidetzky | 607/89 |
| 6,358,272 | B1 * | 3/2002 | Wilden | 607/89 |
| 6,965,085 | B1 * | 11/2005 | Orrico et al. | 200/314 |
| 2006/0129211 | A1 | 6/2006 | Canitano et al. | |
| 2007/0198004 | A1 | 8/2007 | Altshuler et al. | |
| 2008/0004608 | A1 | 1/2008 | Dacquay et al. | |

FOREIGN PATENT DOCUMENTS

CN     201002443 Y  *  1/2008

OTHER PUBLICATIONS

Patent Cooperation Treaty, International Search Authority, International Search Report and Written Opinion, Mailed Aug. 25, 2011, International Application No. PCT/IB2011/00240.
US Patent and Trademark Office; Non-Final Office Action for U.S. Appl. No. 13/521,224 dated Apr. 2, 2013.

* cited by examiner

*Primary Examiner* — Lynsey Crandall
(74) *Attorney, Agent, or Firm* — Parsons Behle & Latimer

(57) ABSTRACT

A system includes a LLLT device, with a laser diode and a momentary switch, and a clip device configured to attach to the LLLT device and to press the momentary switch while attached, causing the LLLT device to activate the laser diode. A LLLT device includes a laser diode, a front end from which light radiates when the laser diode is activated, and an eye safety mechanism at the front end. The LLLT device is configured to activate the laser diode when the front end is pressed.

21 Claims, 4 Drawing Sheets

LOW LEVEL LASER THERAPY (LLLT) SYSTEMS AND DEVICES

RELATED APPLICATION DATA

The present application is a continuation-in-part of U.S. patent application Ser. No. 12/534,878 filed Aug. 4, 2009 now U.S. Pat. No. 8,790,382, entitled Handheld Low-Level Laser Therapy Apparatus, which is incorporated herein by reference in its entirety, and claims the benefit of priority under 35 U.S.C. §119 to U.S. Provisional Application No. 61/295,039 filed Jan. 14, 2010, entitled Eye Safety and Comfort Mechanism For a Handheld Low Level Laser Therapy (LLLT) Device, which is incorporated herein by reference in its entirety.

SUMMARY

An embodiment of the present application relates to an apparatus and method for treating people, using a low level laser therapy (LLLT) device. The device may be handheld and include a laser diode that provides a monochromatic single phased laser beam that disperses with a small angle (e.g., between about 5-7 degrees) in one direction and with a larger angle (e.g., between about 30-40 degrees) in a direction perpendicular to the first direction. The device may exploit the natural divergence of the laser diode, to produce a light beam that illuminates a larger area simultaneously with a monochromatic, essentially coherent and collimated light beam.

The device includes a lens that turns the laser beam into a collimated beam wherein the rays from the smaller dispersion angle provide a narrow illumination area, and the rays from the larger dispersion angle provide an elongated illumination area. Optionally, the elongated illumination area is at least twice the size of the narrow illumination area. In some embodiments, the illumination area forms a rectangular area. Alternatively, the illumination area forms an ellipsoidal area. Optionally, the beam provides eye safety as a result of the dispersion, which provides less intensity per unit area.

In some embodiments, the monochromatic laser beam is an invisible infrared beam. Optionally, the wavelength of the laser beam is between about 800 to 900 nm. In an embodiment, a visible light source (e.g., an LED) is used to provide a supplementary visible light beam to accompany the invisible light beam so that a user will be able to see that the device is active and will not point the device towards his eyes. In some embodiments, the visible light beam coincides with the invisible laser beam. Alternatively, the visible light beam illuminates an area that surrounds the laser beam, forming a frame around the invisible laser beam to enhance user safety.

An alternative operation mechanism is a momentary, push-button switch that may be held down to keep the laser activated and to avoid activation and then incautious movement of the device, accidentally aiming the laser beam toward the eye.

However, the holding of a momentary, push-button switch during treatment might not be convenient and might not be needed for sufficient eye safety when the treatment is in an area far from the eye (e.g., back, knee, etc.).

To address this problem, a clip device, which is a separate part from the LLLT device, can be provided to users along with the LLLT device. The clip device can be attached to the LLLT and hold the momentary, push-button switch continuously in an activated position. This method provides a convenient solution for both the eye safety requirement and convenience of use to the patient.

BRIEF DESCRIPTION OF FIGURES

Like reference numbers and designations in the various drawings indicate like elements.

DETAILED DESCRIPTION

In the following description, reference is made to the accompanying drawings that form a part thereof, and in which is shown by way of illustration specific embodiments in which the invention may be practiced. These embodiments are described in sufficient detail to enable those skilled in the art to practice the invention, and it is to be understood that modifications to the various disclosed embodiments may be made, and other embodiments may be utilized, without departing from the spirit and scope of the present invention. The following detailed description is, therefore, not to be taken in a limiting sense.

In an embodiment, a system includes a LLLT device with a laser diode and a momentary switch, the LLLT device being configured to activate the laser diode when the momentary switch is pressed. A clip device is configured to attach to the LLLT device and to press the momentary switch while attached, causing the LLLT device to activate the laser diode.

As an example, the LLLT device may further include an encasement encasing the laser diode, the encasement having a first side and an opposing second side. The momentary switch may be located at the first side and the clip device configured to contact both the momentary switch and the opposing second side while attached. A variety of types of known momentary switches may be used, such as a momentary, push-button switch, as opposed to toggle, rocker, slide, etc. momentary switches. Also, a switching mechanism of the momentary switch may be configured to close when the momentary switch is pressed. It may be conceivable to instead use a switch that is normally closed until pressed.

Figure 3:
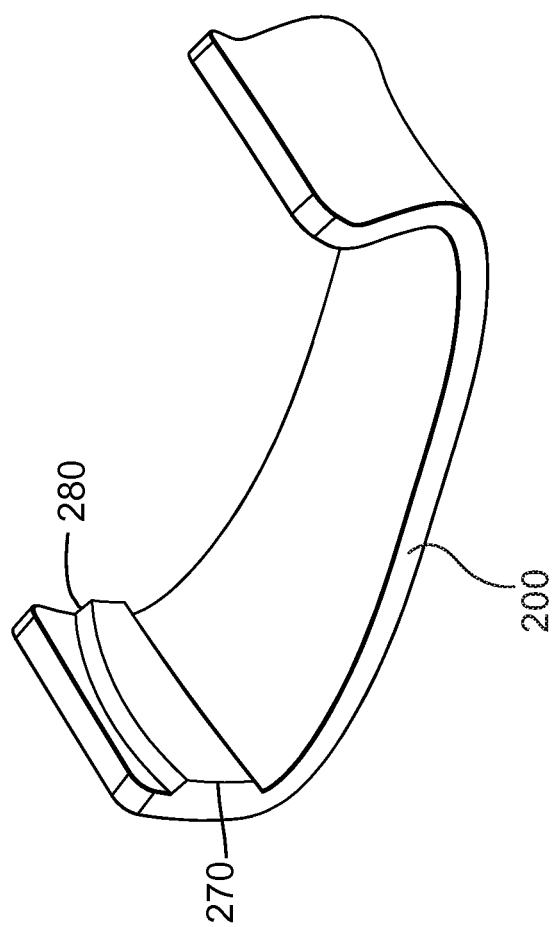
FIG. 3 illustrates a clip device which can press the momentary, push-button switch.

The clip device may have substantially a U-shape with opposing sides and a bottom connecting the opposing sides. The momentary, push-button switch may have a button, one of the opposing sides of the clip device having a protrusion with a shape that corresponds to a shape of a recess into the button. The protrusion may be configured to enter the recess and to press the momentary switch while the clip is attached to the LLLT device. For example, the protrusion may be a mesa 270 having one or more beveled edge 280, such as shown in FIG. 3, and the button may have a corresponding recess, such as shown for the button of momentary switch 430 in FIG. 4. Also, while attached to the LLLT device, the clip device may require user manipulation to be removed. That is, once attached, the clip device may remain attached until a user takes action to remove it, as opposed to a clip device that operates to press the momentary switch, but is held in place by a user.

Also, by way of example, the LLLT device may be configured such that the activation of the laser diode while the clip device is attached includes activation of the laser diode continuously until the clip device is removed. As an alternative, the LLLT device may include a deactivation timer and be configured such that the activation of the laser diode while the clip device is attached provides activation of the laser diode continuously until the timer deactivates the laser diode.

Accordingly, in another embodiment, a system includes a LLLT device with a laser diode, a momentary, push-button switch having a button with a recess therein, electronic circuitry operatively integrating the momentary, push-button switch to activate the laser diode when the momentary, push-button switch is pressed, and an encasement encasing the laser diode. The encasement has a first side and an opposing second side, the momentary, push-button switch being located at the first side. The system includes a clip device configured to attach to the LLLT device and to contact both the momentary, push-button switch and the second side of the encasement while attached. The clip device includes substantially a U-shape having a first side, an opposing second side, and a bottom connecting the first side and the second side. The first side of the clip device has a protrusion with a shape that corresponds to a shape of the recess in the button. The protrusion enters the recess and presses the momentary switch while the clip device is attached, causing the LLLT device to activate the laser diode. The second side of the clip device contacts the second side of the encasement while attached. Also, while attached, the clip device requires user manipulation to be removed.

Thus, as may be understood from the description herein, a further embodiment provides a method that includes providing a LLLT device with a laser diode and a momentary switch, the LLLT device being configured to activate the laser diode when the momentary switch is pressed, and attaching a clip device to the LLLT device. The method includes pressing the momentary switch using only the clip device while it is attached, causing the LLLT device to activate the laser diode.

Figure 1:
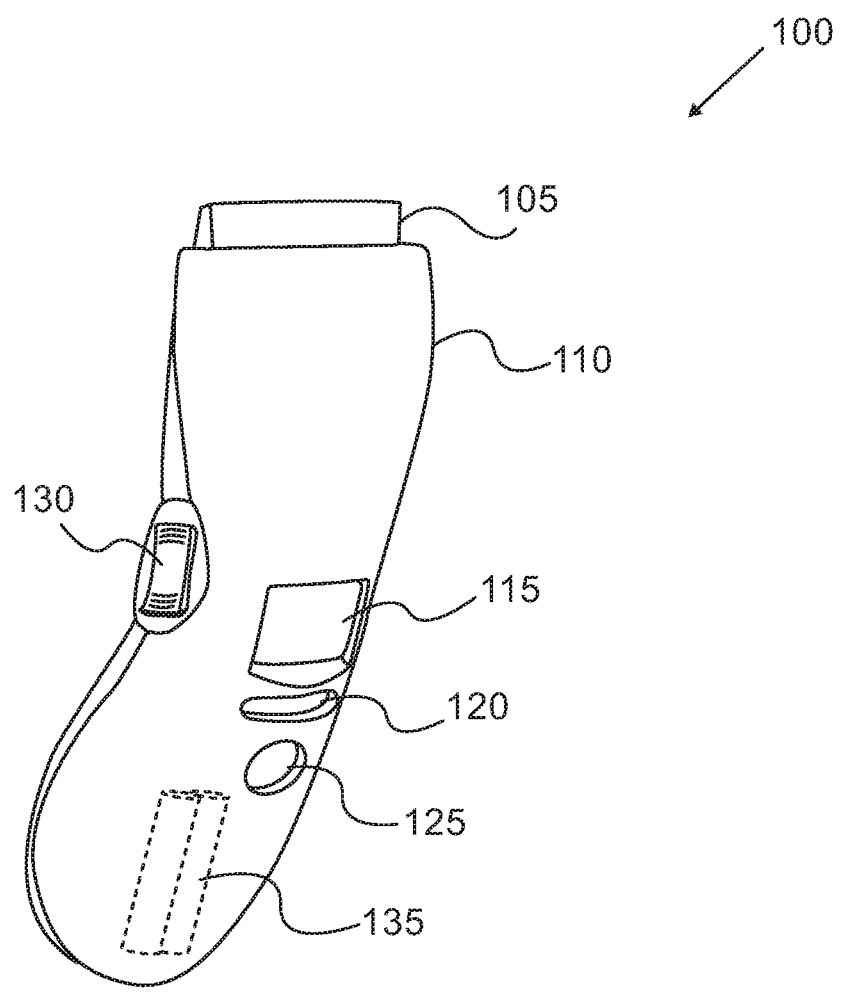
FIG. 1 is a schematic illustration of a handheld LLLT device with an eye safety mechanism and a momentary, push-button switch.

FIG. 1 is a schematic illustration of an LLLT device 100 with an eye safety mechanism and momentary, push-button switch for performing laser therapy, according to an embodiment of the present application. In the embodiment shown, the light sources and electronic circuitry for powering device 100 are encased in an ergonomic encasement 110 designed to fit into a user's hand. Even so, features described herein of the various embodiments may also be applicable to LLLT devices that are not hand held. Optionally, device 100 includes an on/off switch 125, which turns device 100 on and off. When device 100 is in the on state, it may be activated by pressing on momentary, push-button switch 130 located on the side of encasement 110. Alternatively or additionally, device 100 may be activated by pushing eye safety activation switches 105 against the person or object being radiated, when using device 100. Activation when pressing against the person being radiated increases the safety of device 100, since it will not allow a user accidentally to shine light into the user's eye. In some cases, pressing against the user's skin is advantageous since it may reduce blood flow and enhance efficiency of the light absorption. Alternatively, in some cases, the user may have a wound and it is preferable not to press against the user's skin.

In some embodiments, device 100 is powered by an internal power source (e.g., batteries 135). Alternatively or additionally, device 100 can be powered by an external power source via a power-cable (not shown) that is plugged into an external power source, such as a household power socket. Optionally, when device 100 is plugged into an external power source, batteries 135 may be recharged.

In some embodiments, device 100 includes a display 115, for example an LCD display, which shows a variety of information, such as the status of the battery, and/or a timer/counter. In an embodiment, the timer on display 115 is set by the user to a pre-selected value using a selector 120. The value may represent an amount of time in seconds during which device 100 will remain active when activated by the user. The device 100 will count down and deactivate device 100 automatically once it counts the pre-selected amount of time. For example, if the user wishes to illuminate an area for a specific amount of time, he sets the timer with the desired amount of time and activates device 100. Depending on the mode of activation, as further described herein, device 100 will illuminate the area until the time runs out. That is, described safety mechanisms might function to deactivate device 100 before the time runs out.

FIG. 3 illustrates a clip device 200 which can hold the momentary, push-button switch 130. Clip 200 can be made of flexible plastic material, such as polycarbonate produced by injection molding. When attached to LLLT device 100 of FIG. 1, clip 200 is continuously pushing momentary, push-button switch 130 of FIG. 1 due to its flexibility.

Figure 4:
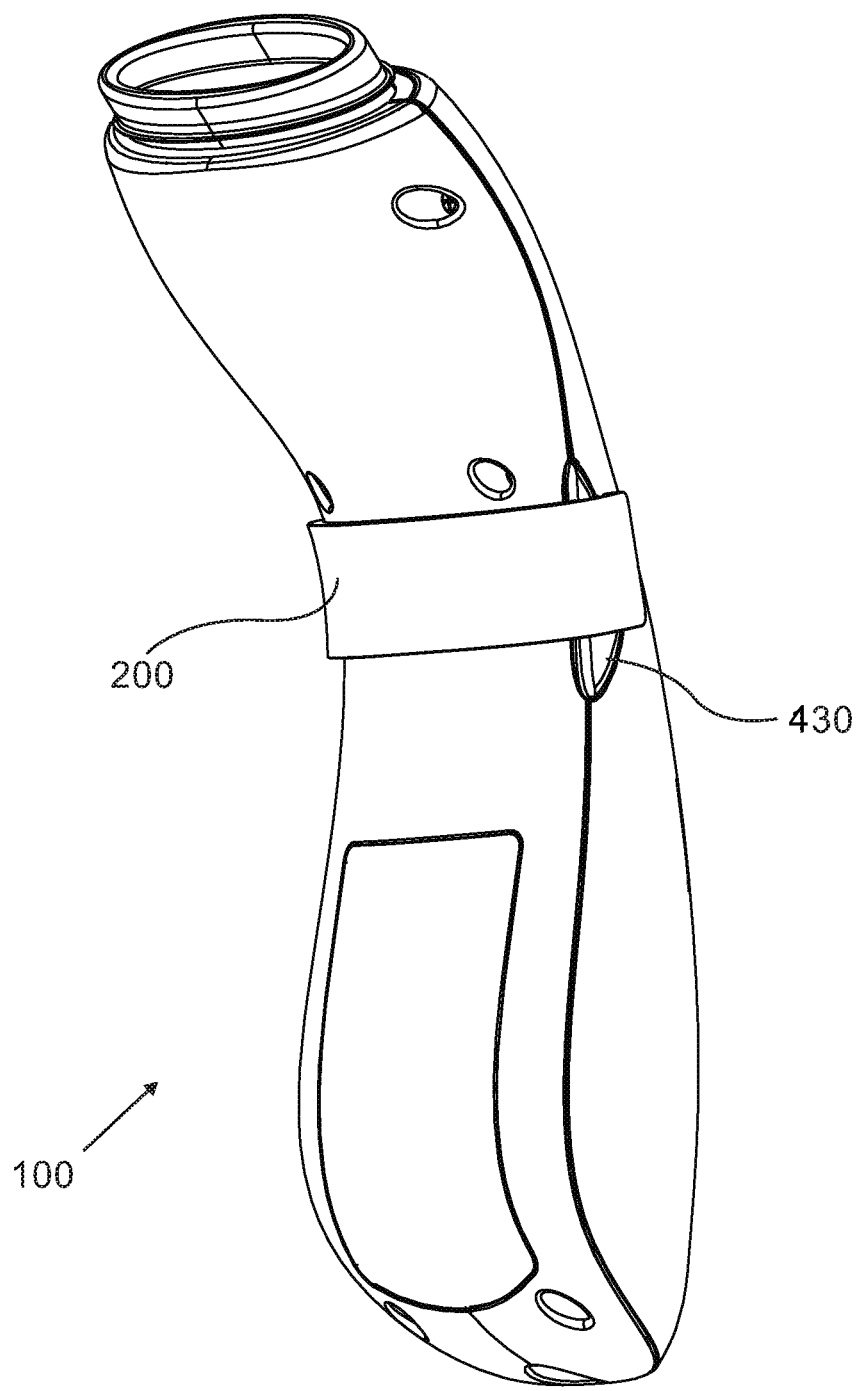
FIG. 4 shows the LLLT device of FIG. 1 with the clip device of FIG. 3 attached to it.

FIG. 4 shows LLLT device 100 of FIG. 1 with clip device 200 of FIG. 3 attached to it. When LLLT device 100 is turned on by using switch 125 of FIG. 1, and the required treatment time is set by selector 120 of FIG. 1, the flexible clip 200, when attached to LLLT device 100 continuously pushes momentary, push-button switch 130, activating the laser continuously for a pre-set time, for the convenience of use. When the clip 200 is removed, the laser will not activate unless the push-button switch 130 is held down the whole time, to provide eye safety.

According to another embodiment, a LLLT device includes a laser diode, a front end from which light radiates when the laser diode is activated, and an eye safety mechanism at the front end. The LLLT device is configured to activate the laser diode when the front end is pressed.

By way of example, the eye safety mechanism may form a frontmost part of the front end of the LLLT device, the LLLT device being configured to activate the laser diode when the frontmost part is pressed against a part to be treated of a patient's body. The eye safety mechanism may have at least one spring-mounted guide rod extending into the LLLT device and at least one momentary, push-button switch aligned to be pressed by the guide rod when the front end is pressed, causing the LLLT device to activate the laser diode. The momentary, push-button switch may be a momentary, push-button microswitch or other types of known switches, such as discussed above.

The eye safety mechanism may include two spring-mounted guide rods extending into the LLLT device and two momentary, push-button switches each aligned to be pressed by one of the guide rods when the front end is pressed, causing the LLLT device to activate the laser diode while both switches are pressed. Since an LLLT device may further include an encasement encasing the laser diode, as discussed above, the front end of the LLLT device may extend outside the encasement, but retract at least partially into the encasement when the front end is pressed.

Accordingly, in another embodiment, an LLLT device includes a laser diode, a front end from which light radiates when the laser diode is activated, and an eye safety mechanism providing a frontmost part of the front end. The eye safety mechanism includes two spring-mounted guide rods extending into the LLLT device, and two momentary, push-button microswitches each aligned to be pressed by one of the guide rods when the frontmost part is pressed against a part to be treated of a patient's body. Electronic circuitry operatively integrates the momentary, push-button microswitches to activate the laser diode while both switches are pressed. An encasement encases the laser diode and the front end extends outside the encasement, but retracts at least partially into the encasement when the frontmost part is pressed.

Thus, as may be understood from the description herein, a further embodiment presents a method that includes providing a LLLT device with a laser diode, a front end from which light radiates when the laser diode is activated, and an eye safety mechanism at the front end, the LLLT device being configured to activate the laser diode when the front end is pressed. The method includes pressing the front end against a part to be treated of a patient's body, causing the LLLT device to activate the laser diode.

Figure 2:
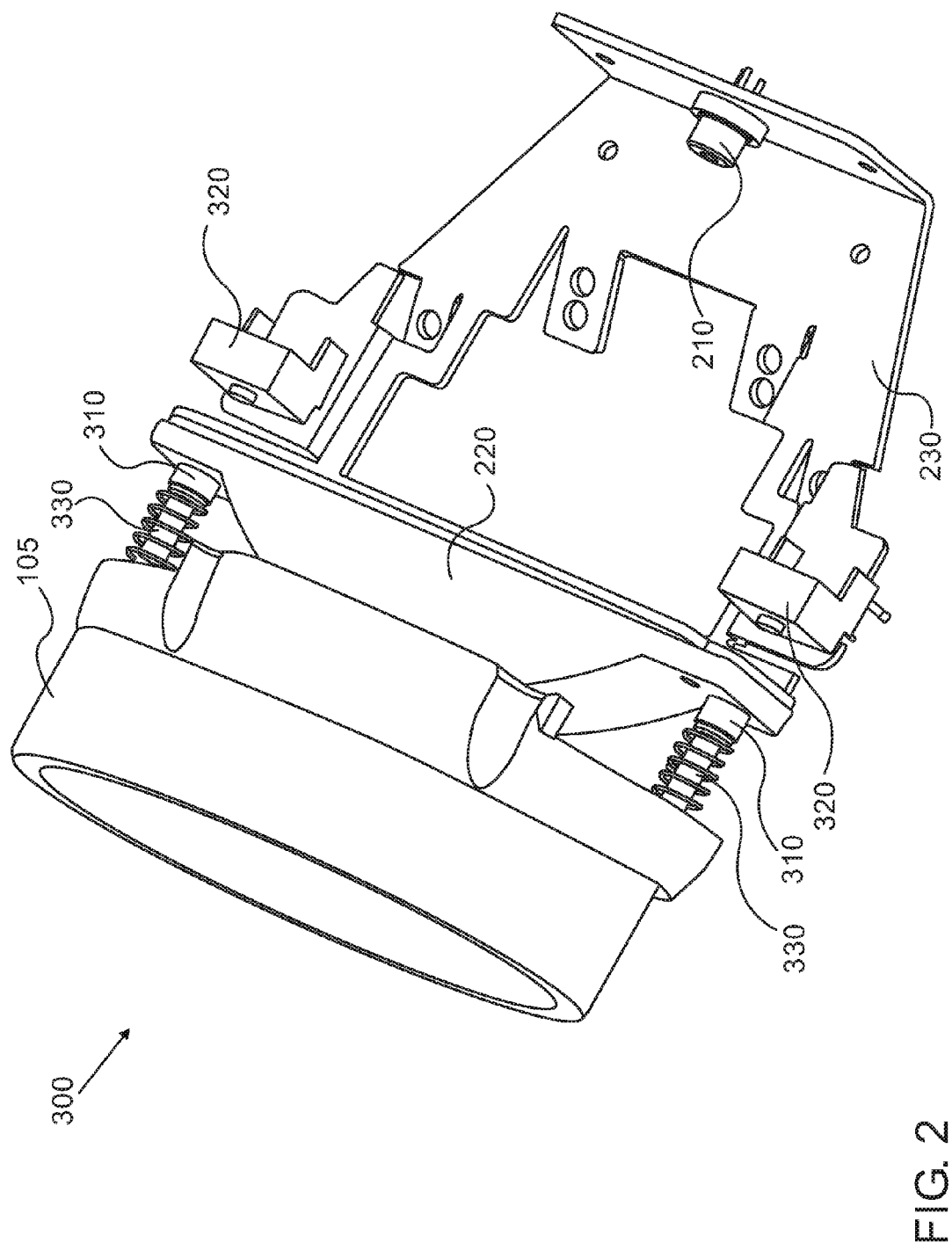
FIG. 2 is a three-dimensional drawing of an eye safety mechanism suitable for use with the LLLT device of FIG. 1.

FIG. 2 is a schematic illustration of an internal structure for manufacturing device 100 with an eye safety mechanism 300, according to an embodiment of the present application. As mentioned above, when device 100 is turned on, it can be activated by pressing eye safety activation switch 105 against the body of the patient. Optionally, eye safety activation switch 105 is connected to two sliders 310, and two spring-mounted guide rods 330 are inserted into sliders 310, one on each side. When eye safety activation switch 105 is pushed into encasement 110 of FIG. 1, guide rods 330 are moved inward and press two micro-switches 320, which activate a laser diode 210. Components of eye safety mechanism 300 are mounted on a base 230, which may in turn be mounted within encasement 110 shown in FIG. 1. As a result, eye safety activation switch 105 provides a frontmost part of a front end of LLLT device 100 and retracts at least partially into encasement 110 when the frontmost part is pressed against a patient's body. The use of eye safety activation switch 105 prevents the user from activating laser diode 210 and aiming it towards his eyes or the eyes of another person.

Laser diode 210 may be selected to emit infra-red radiation with a monochromatic wave length between 800-900 nm and a power output of at least 100 mw, so that it will be effective in healing the user. Optionally, the wavelength is selected to have optimal performance in providing power to the biological cells of the user, thus it is possible that other wavelengths may be used (e.g. visible light or ultra-violet light) if found to be more effective in dealing with a specific ailment. Additionally, laser diode 210 may be selected having a stronger or weaker power output. Optionally, a lens 220 is placed opposite laser diode 210 to make use of the natural divergence of the laser beam produced by laser diode 210 by collimating the dispersing laser beam and forming an illumination of the elongated monochromatic coherent laser beam on the skin of the user.

Lens 220 may be a toroidal lens having a different lens radius in two directions, so that the diverging beam formed from laser diode 210 will extend perpendicular to the lens and form an elongated illumination from a monochromatic coherent laser beam. Lens 210 may have a rectangular or ellipsoidal shape and create a rectangular or ellipsoidal illumination. Alternatively or additionally, lens 210 may be a single lens, a double lens or any other combination of lenses as long as it produces the elongated monochromatic coherent laser beam to radiate the user. Optionally, elements other than lenses may affect the unity of phase and direction of the coherent laser beam.

Although this invention has been described in terms of certain preferred embodiments, other embodiments that are apparent to those of ordinary skill in the art, including embodiments that do not provide all of the features and advantages set forth herein, are also within the scope of this invention.

What is claimed is:

1. A system comprising:
a low-level laser therapy (LLLT) device including a laser diode, a momentary switch, and an encasement encasing the laser diode, the encasement having a first side and an opposing second side, the momentary switch being located at the first side and the LLLT device being configured to activate the laser diode when the momentary switch is pressed; and
a completely detachable clip device separated from but configured to attach to the LLLT device and to press the momentary switch without user manipulation while attached, causing the LLLT device to activate the laser diode, and further configured to detach and separate from the LLLT device and to release the momentary switch while detached, the clip device further being flexible and configured to continuously contact both the momentary switch and the second side of the encasement while attached, the clip device being attached to the LLLT device solely by contact with the momentary switch and the opposing second side.

2. The system of claim 1 wherein the clip device being further configured to release the momentary switch solely by detaching the clip device.

3. The system of claim 1 wherein momentary switch comprises a momentary, push-button switch and the LLLT device is further configured to activate the laser diode when the momentary, push-button switch is pressed without the detachable clip.

4. The system of claim 2 wherein the clip device comprises substantially a U-shape having opposing sides and a bottom connecting the opposing sides and wherein the momentary, push-button switch comprises a button, one of the opposing sides of the clip device having a protrusion with a shape that corresponds to a shape of a recess into the button, the protrusion being configured to enter the recess and to press the momentary switch while the clip is attached to the LLLT device.

5. The system of claim 4 wherein the protrusion comprises a mesa having one or more beveled edge, the mesa restricting movement of the side of the clip device having the protrusion in a direction other than normal to the momentary, push-button switch while the clip device is attached to the LLLT device.

6. The system of claim 1 wherein, while attached to the LLLT device, the clip device requires user manipulation to be removed.

7. The system of claim 1 wherein the LLLT device is configured such that the activation of the laser diode while the clip device is attached comprises activation of the laser diode continuously until the clip device is removed.

8. The system of claim 1 wherein the LLLT device further comprises a deactivation timer, the LLLT device being configured such that the activation of the laser diode while the clip device is attached comprises activation of the laser diode continuously until the timer deactivates the laser diode.

9. The system of claim 1 wherein a switching mechanism of the momentary switch is configured to close when the momentary switch is pressed.

10. A system comprising:
a LLLT device including a laser diode, a momentary, push-button switch having a button with a recess therein, electronic circuitry operatively integrating the momentary, push-button switch to activate the laser diode when the momentary, push-button switch is pressed, and an encasement encasing the laser diode, the encasement having a first side and an opposing second side, the momentary, push-button switch being located at the first side;

a completely detachable clip device separated from but configured to attach to the LLLT device and to continuously contact both the momentary, push-button switch and the second side of the encasement while attached, the clip device being attached to the LLLT device solely by contact with the momentary switch and the second side of the encasement, the clip device including substantially a U-shape having a first side, an opposing second side, and a bottom connecting the first side and the second side, the first side of the clip device having a protrusion with a shape that corresponds to a shape of the recess in the button, the protrusion entering the recess and pressing the momentary switch without user manipulation while the clip device is attached and the clip device being configured to release the momentary switch solely by detaching the clip, causing the LLLT device to activate the laser diode, the second side of the clip device contacting the second side of the encasement while attached, and, while attached, the clip device requiring user manipulation to be removed, and the clip device being further configured to detach and separate from the LLLT device and to release the momentary switch while detached;

the LLLT device being further configured to activate the laser diode when the momentary, push-button switch is pressed without the detachable clip; and the LLLT device further including:
a front end from which light radiates when the laser diode is activated; and
an eye safety mechanism at the front end, the LLLT device being still further configured to activate the laser diode when the front end is pressed.

11. The system of claim 1 wherein the LLLT device further comprises:
a front end from which light radiates when the laser diode is activated; and
an eye safety mechanism at the front end, the LLLT device being additionally configured to activate the laser diode when the front end is pressed.

12. The system of claim 11 wherein eye safety mechanism comprises a frontmost part of the front end of the LLLT device, the LLLT device being configured to activate the laser diode when the frontmost part is pressed against a part to be treated of a patient's body.

13. The LLLT device of claim 11 wherein the eye safety mechanism comprises at least one spring-mounted guide rod extending into the LLLT device and at least one other momentary, push-button switch aligned to be pressed by the guide rod when the front end is pressed, causing the LLLT device to activate the laser diode.

14. The LLLT device of claim 13 wherein the other momentary, push-button switch comprises a momentary, push-button microswitch.

15. The LLLT device of claim 13 wherein a switching mechanism of the other momentary, push-button switch is configured to close when the momentary, push-button switch is pressed.

16. The LLLT device of claim 11 wherein the eye safety mechanism comprises two spring-mounted guide rods extending into the LLLT device and two other momentary, push-button switches each aligned to be pressed by one of the guide rods when the front end is pressed, causing the LLLT device to activate the laser diode while both of the other switches are pressed.

17. The LLLT device of claim 11 wherein the LLLT device further comprises an encasement encasing the laser diode, the front end of the LLLT device extending outside the encasement, but retracting at least partially into the encasement when the front end is pressed.

18. The system of claim 10 wherein the protrusion comprises a mesa having one or more beveled edge, the mesa restricting movement of the side of the clip device having the protrusion in a direction other than normal to the momentary, push-button switch while the clip device is attached to the LLLT device.

19. The system of claim 10 wherein the LLLT device is configured such that the activation of the laser diode while the clip device is attached comprises activation of the laser diode continuously until the clip device is removed.

20. The system of claim 10 wherein the LLLT device further comprises a deactivation timer, the LLLT device being configured such that the activation of the laser diode while the clip device is attached comprises activation of the laser diode continuously until the timer deactivates the laser diode.

21. The system of claim 10 wherein a switching mechanism of the momentary switch is configured to close when the momentary switch is pressed.

* * * * *